(12) United States Patent
Meskens (10) Patent No.: US 10,556,110 B2
(45) Date of Patent: Feb. 11, 2020

(54) EXTERNAL UNIT OF AN IMPLANTED MEDICAL DEVICE

(71) Applicant: Cochlear Limited, Macquarie University, NSW (AU)

(72) Inventor: Werner Meskens, Opwijk (BE)

(73) Assignee: Cochlear Limited, Macquarie University, NSW (AU)

( * ) Notice: Subject to any disclaimer, the term of this patent is extended or adjusted under 35 U.S.C. 154(b) by 22 days.

(21) Appl. No.: 15/817,604

(22) Filed: Nov. 20, 2017

(65) Prior Publication Data

US 2018/0071533 A1    Mar. 15, 2018

Related U.S. Application Data

(63) Continuation of application No. 15/232,433, filed on Aug. 9, 2016, now abandoned, which is a continuation of application No. 13/678,533, filed on Nov. 15, 2012, now abandoned.

(51) Int. Cl.
| | |
|---|---|
| *A61N 1/37* | (2006.01) |
| *A61N 1/36* | (2006.01) |
| *A61N 1/05* | (2006.01) |
| *A61N 1/372* | (2006.01) |

(52) U.S. Cl.
CPC ....... *A61N 1/36036* (2017.08); *A61N 1/0541* (2013.01); *A61N 1/37252* (2013.01)

(58) Field of Classification Search
CPC ............ A61N 1/36032; A61N 1/37252; A61N 1/0541
See application file for complete search history.

(56) References Cited

U.S. PATENT DOCUMENTS

| | | | |
|---|---|---|---|
| 5,304,209 A | 4/1994 | Adams et al. | |
| 7,599,508 B1 | 10/2009 | Lynch et al. | |
| 7,818,066 B1 | 10/2010 | Palmer | |
| 7,860,574 B2 | 12/2010 | Von Arx et al. | |
| 8,554,329 B1 | 10/2013 | Mann et al. | |
| 8,707,245 B2 | 4/2014 | Case et al. | |
| 2007/0106344 A1 | 5/2007 | Darley et al. | |
| 2010/0046778 A1 | 2/2010 | Crawford et al. | |
| 2011/0046730 A1* | 2/2011 | Meskens | A61N 1/36036 623/10 |
| 2012/0022613 A1 | 1/2012 | Meskens | |
| 2012/0232616 A1* | 9/2012 | Van Baelen | A61N 1/37217 607/57 |
| 2013/0109909 A1 | 5/2013 | Van Gerwen et al. | |

FOREIGN PATENT DOCUMENTS

| | | |
|---|---|---|
| WO | 2007146773 | 12/2007 |
| WO | 2009056167 | 5/2009 |
| WO | 2010017118 | 2/2010 |

\* cited by examiner

*Primary Examiner* — Rex R Holmes
(74) *Attorney, Agent, or Firm* — Edell, Shapiro & Finnan, LLC (57) ABSTRACT

A method, systems, and devices are disclosed. An example method includes determining whether an external unit of an implanted medical device is coupled to an implanted unit of the implanted medical device. In response to determining that the external unit is coupled to the implanted unit, the example method includes causing the external unit to operate in a first operating mode. In response to determining that the external unit is not coupled to the implanted unit, the example method includes causing the external unit to operate in a second operating mode.

23 Claims, 7 Drawing Sheets

EXTERNAL UNIT OF AN IMPLANTED MEDICAL DEVICE

REFERENCE TO RELATED APPLICATION

The present application is a continuation of U.S. patent application Ser. No. 15/232,433, filed Aug. 9, 2016, now Abandoned, which is in turn a continuation of U.S. patent application Ser. No. 13/678,533, filed Nov. 15, 2012, now Abandoned. The entirety of each of these applications is incorporated herein by reference.

BACKGROUND

Individuals who suffer from certain medical conditions may benefit from the use of an implanted medical device. Depending on the type and the severity of the medical condition, an individual can employ a partially implanted medical device or a totally implanted medical device. Partially implanted medical devices typically include an external unit that performs at least some processing functions and an implanted unit that at least delivers a stimulus to a body part of a user, such as an organ. In the case of a totally implantable medical device, the entire device is implanted in the body of a user. Additionally, the implanted medical device is often configured to communicate with a remote device that allows an individual to adjust a component or a function of the implanted medical device.

SUMMARY

A method is disclosed. The method includes determining whether an external unit of an implanted medical device is coupled to an implanted unit of the implanted medical device. In response to determining that the external unit is coupled to the implanted unit, the method includes causing the external unit to operate in a first operating mode. In response to determining that the external unit is not coupled to the implanted unit, the method includes causing the external unit to operate in a second operating mode.

A system is disclosed. The system includes an implanted unit of a hearing prosthesis that is configured to deliver a stimulus to a recipient. The system also includes an external unit of a hearing prosthesis. The external unit is configured to generate and send at least a power signal to the implanted unit via a first communication channel in a first operating mode. The external unit is further configured to send a command signal to an electronic device via a second communication channel when operating in a second operating mode. The command signal includes instruction for causing the electronic device to perform a function.

A non-transitory computer-readable memory is disclosed. The non-transitory computer-readable memory includes instructions executable by a processor to cause the processor to perform functions. The functions include determining a range between an implanted unit of a hearing prosthesis and an external unit of a hearing prosthesis. The functions further include causing the external unit to send a first signal to the implanted unit upon determining that the range is below a threshold range. The functions additionally include causing the external unit to send a second signal to an electronic device upon determining that the range is above the threshold range.

A device is disclosed. The device includes an inductive coil configured to inductively transfer at least a power signal to an implanted unit. The device further includes a power supply configured to provide the power signal. The device also includes a user interface configured to receive an input signal. The device additionally includes an antenna and a transceiver. The transceiver is configured to transmit a control signal to an electronic device via the antenna. The device further includes a processor. The processor is configured to determine an operating mode. In response to determining that the operating mode is a first operating mode, the processor is configured to cause the power supply to provide the power signal to the inductive coil in response to determining that the operating mode is the first operating mode. The processor is additionally configured to receive an input signal from a user interface, generate a command signal that includes information indicative of the input signal, and cause the transceiver to transmit a command signal to an electronic device in response to determining that the operating mode is a second operating mode.

These as well as other aspects and advantages will become apparent to those of ordinary skill in the art by reading the following detailed description, with reference where appropriate to the accompanying drawings. Further, it is understood that this summary is merely an example and is not intended to limit the scope of the invention as claimed.

BRIEF DESCRIPTION OF THE FIGURES

Presently preferred embodiments are described below in conjunction with the appended drawing figures, wherein like reference numerals refer to like elements in the various figures, and wherein.

DETAILED DESCRIPTION

The following detailed description describes various features, functions, and attributes of the disclosed systems, methods, and devices with reference to the accompanying figures. In the figures, similar symbols typically identify similar components, unless context dictates otherwise. The illustrative embodiments described herein are not meant to be limiting. It will be readily understood that the aspects of the present disclosure, as generally described herein, and illustrated in the figures, can be arranged, substituted, combined, separated, and designed in a wide variety of different configurations, all of which are contemplated herein.

Figure 1A:
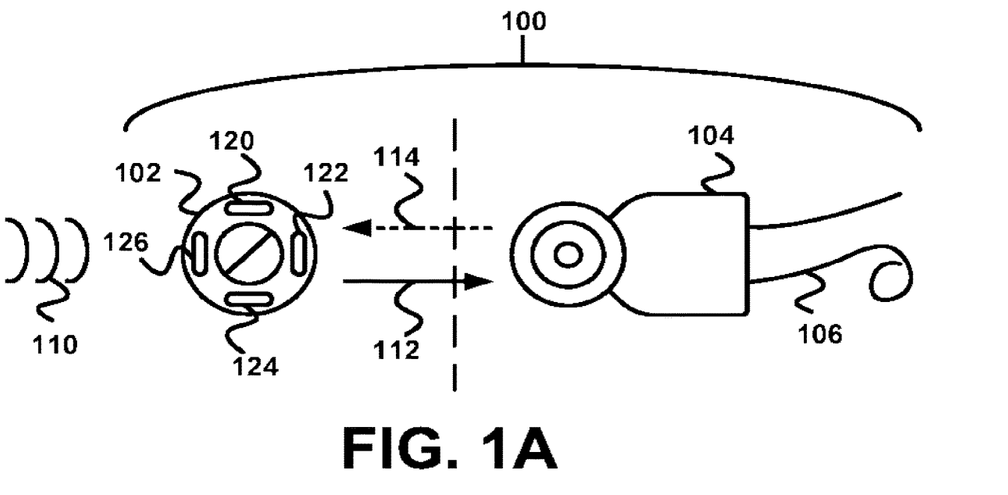
FIG. 1A illustrates a first example hearing prosthesis, according to an example.
Figure 1B:
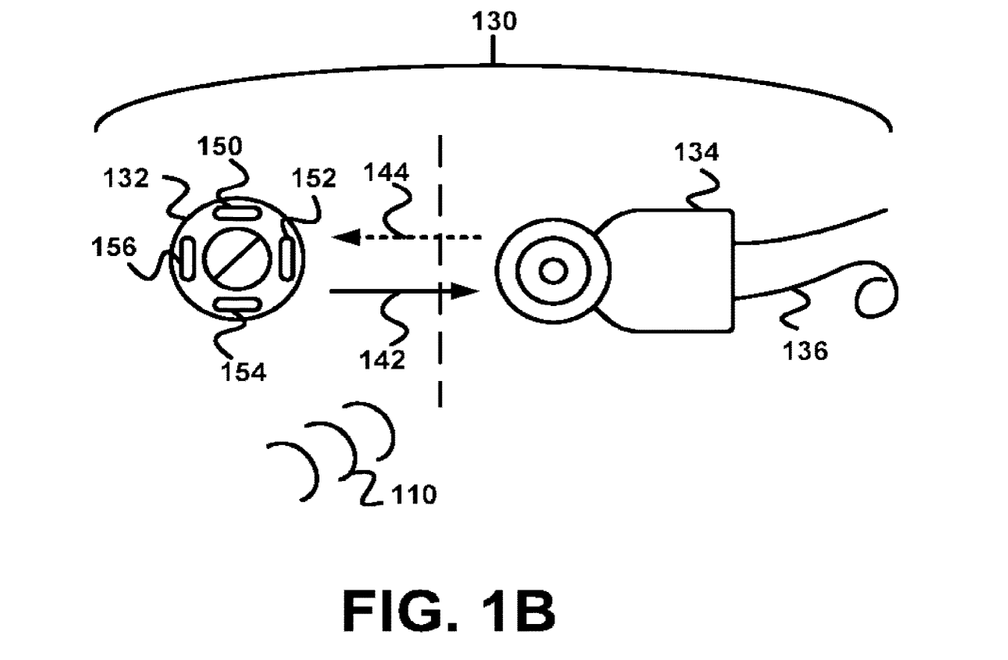
FIG. 1B illustrates a second example hearing prosthesis, according to an example.

FIGS. 1A and 1B illustrate example hearing prostheses 100, 130. The hearing prostheses 100, 130 are two examples of implanted medical devices that include an external unit and an implanted unit. A recipient utilizes one of the hearing prostheses 100, 130 to assist the recipient in perceiving at least a portion of a sound. FIG. 1A illustrates a hearing prosthesis 100. The hearing prosthesis 100 includes an external unit 102 and an implanted unit 104. In FIG. 1A, the hearing prosthesis 100 is a partially implantable cochlear implant. The implanted unit 104 is implanted in the recipient's head such that a portion of the implanted unit 104 is anchored to the recipient's skull. An electrode array 106, which includes one or more electrodes, is implanted in a cochlea of the recipient.

The external unit 102 is worn external to the recipient's body. In one example, the external unit 102 is magnetically secured to the recipient's body. In this example, the external unit 102 and the implanted unit 104 each include one or more magnets. When the external unit 102 is placed over a portion of the recipient's body at which the implanted unit 104 is implanted, the magnets create a magnetic field that secures the external unit 102 to the recipient's body. In another example, the external unit 102 is secured to the recipient's body using any component or series of components suitable for securing the external unit 102 to the recipient's body.

The external unit 102 is configured to generate a stimulation signal that allows the recipient to perceive at least a portion of a sound 110. In one example, the sound 110 originates from a source in an environment. In another example, the sound 110 originates from an external device configured to send a sound signal to the external unit 102, such as an audio streaming device. The external unit 102 includes one or more components configured to receive and processes the sound 110, and the external unit 102 generates a stimulation signal based on the sound 110.

The external unit 102 also provides a power signal to the implanted unit 104. The external unit 102 modulates the power signal based on the stimulation signal such that a modulated power signal 112 contains both the power signal and the stimulation signal. In one example, the external unit 102 inductively transfers the modulated power signal 112 to the implanted unit 104 via a reactive near-field communication channel. In another example, the external unit 102 transmits the modulated power signal 112 using any transmission technique now known or later discovered that is suitable for transferring data and power to the implanted unit 104.

Additionally, the external unit 102 is configured to receive an input from the recipient. The external unit 102 receives the input via one or more of buttons 120-126. The buttons 120-126 are components of a user interface component of the external unit 102. In another example, the external unit 102 includes more or fewer buttons. In yet another example, the user interface component of the external unit 102 includes a different and/or an additional component, such as, for example, a touch screen or a pressure-sensitive pad.

The implanted unit 104 receives the modulated power signal 112 and separates the modulated power signal 112 into the stimulation signal and the power signal. The implanted unit 104 generates an electrical signal based on the stimulation signal. The implanted unit 104 sends the electrical signal to the electrode array 106, which causes the one or more electrodes included on the electrode array 106 to deliver a stimulus, in the form of one or more electrical stimuli, to the recipient's cochlea. Stimulating the recipient's cochlea causes the recipient to perceive at least a portion of the sound 110.

The implanted unit 104 is also configured to monitor a plurality of parameters associated with generating and delivering the stimulus. The plurality of parameters may include an output voltage, an output current, a line impedance, and/or any other parameter associated with generating and delivering the stimulus. The implanted unit 104 generates a telemetry signal 114 that includes information indicative of one or more parameters of the plurality of parameters.

The implanted unit 104 transmits the telemetry signal 114 to the external unit 102. In one example, the implanted unit 104 inductively transfers the telemetry signal 114 to the external unit 102 via the reactive near-field communication channel. In another example, implanted unit 104 transfers the telemetry signal 114 to the external unit 102 using a different transmission technique. The external unit 102 uses the telemetry signal to verify proper operation of the implanted unit 104, to calibrate the hearing prosthesis 100, and/or for any other suitable purpose in processing sounds.

FIG. 1B illustrates a hearing prosthesis 130. The hearing prosthesis 130 includes an external unit 132 and an implanted unit 134. In FIG. 1B, the hearing prosthesis 130 is a totally implantable hearing prosthesis. The implanted unit 134 is implanted in the recipient's head such that a portion of the implanted unit 134 is anchored to the recipient's skull. An electrode array 126, which is the same as or is substantially similar to the electrode array 106 depicted in FIG. 1A, is implanted in a cochlea of the recipient.

The external unit 132 is worn external to the recipient's body. In one example, the external unit 132 is magnetically secured to the recipient's body. The external unit 132 and the implanted unit 134 each include one or more magnets. When the external unit 132 is placed over a portion of the recipient's body at which the implanted unit 134 is implanted, the magnets create a magnetic field that secures the external unit 132 to the recipient's body. In another example, the external unit 132 is secured to the recipient's body using any component or series of components suitable for securing the external unit 132 to the recipient's body.

The implanted unit 134 includes one or more components configured to process the sound 110. Thus, the implanted unit 134 receives and processes the sound 110, and the implanted unit 134 generates a stimulation signal based on the sound 110. The implanted unit 134 uses the stimulation signal to generate and deliver a stimulus to the recipient's cochlea via the electrode array 126.

The external unit 132 is configured to provide a power signal 142 to the implanted unit 134. The power signal 142 may supply power to one or more components of the implanted unit 134, and/or the power signal 142 may recharge an internal power supply of the implanted unit 134. In one example, the external unit 132 inductively transfers the power signal 142 to the implanted unit 134 via a reactive near-field communication channel. In another example, the external unit 132 transmits the power signal 142 using any transmission technique now known or later discovered that is suitable for transferring data and power to the implanted unit 104.

Like the external unit 102, the external unit 132 is also configured to receive an input from the recipient. The external unit 132 receives the input via one or more of buttons 150-156. The buttons 150-156 are part of a user interface component of the external unit 132 and are the same as or are substantially similar to the buttons 120-126 described with respect to FIG. 1A. In another example, the external unit 132 includes more or fewer buttons than the buttons 150-156. In yet another example, the user interface component of the external unit 132 includes a different and/or an additional component, such as, for example, a touch screen or a pressure-sensitive pad.

In one example, the external unit 132 does not include a component configured to receive the sound 110. Thus, the external unit 132 does not generate a stimulation signal, and the power signal 142 is not modulated. In another example, the external unit 132 is configured to receive and process the sound 110. In this example, the external unit 132 and the power signal 142 are the same as or are substantially similar to the external unit 102 and the modulated power signal 112, respectively, as depicted in FIG. 1A. Additionally, the implanted unit 134 is configured to utilize the stimulation signal received from the external unit 132 when the power signal 142 is received, and the implanted unit is configured to generate the stimulation signal when the power signal 142 is not received.

Depending on the configuration of the external unit 132, the implanted unit 134 may generate and send a telemetry signal 144 to the external unit 132. The telemetry signal 144 is the same as or is substantially similar to the telemetry signal 114 described with respect to FIG. 1A. For instance, in an example in which the external unit 132 is configured to generate the stimulation signal, the implanted unit 134 sends the telemetry signal 144 to the external unit 134.

In the examples described above, the hearing prostheses 100, 130 are cochlear implants. In an additional example, one or both of the hearing prostheses 100, 130 are bone conduction devices, direct acoustic stimulation devices, auditory brain stem implants, middle ear implants, or any other hearing prostheses or combination of hearing prostheses now known or later developed. In this example, the implanted units 104, 124 each include one or more components that are implanted (or otherwise placed) in one of the recipient's auditory nerves, the brain, and/or any other body part capable of being stimulated to assist the recipient in perceiving at least a portion of a sound. Delivering a stimulus to the body part stimulates the body part, allowing the recipient to perceive at least a portion of one of the sound 110.

Figure 2A:
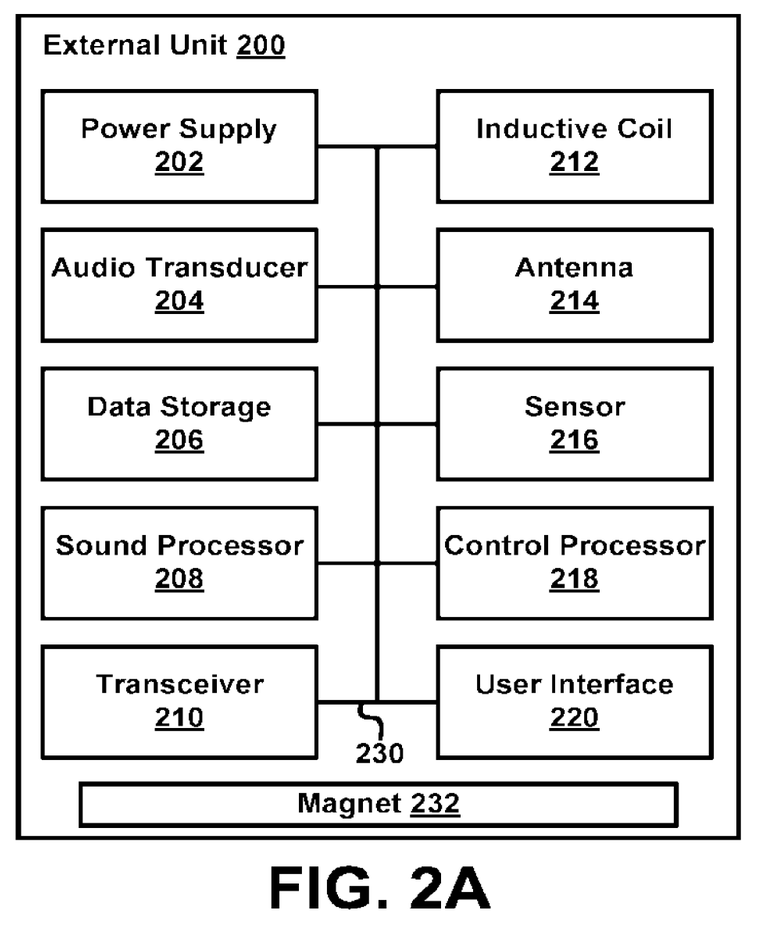
FIG. 2A is a block diagram of an external unit depicted in FIG. 1A, according to an example.

FIG. 2A is a block diagram of an external unit 200. The external unit 200 is one example of the external unit 102 depicted in FIG. 1A. The external unit 200 includes a power supply 202, an audio transducer 204, a data storage 206, a sound processor 208, a transceiver 210, an inductive coil 212, an antenna 214, a sensor 216, a control processor 218, and a user interface 220, all of which may be connected directly or indirectly via circuitry 230. The external unit 200 also includes a magnet 232 that is used to secure the external unit 200 to the recipient's body. For illustrative purposes, the external unit 200 is described as the external unit 102 depicted in FIG. 1A.

The power supply 202 supplies power to the various components of the external unit 200 and can be any suitable power supply, such as a rechargeable or a non-rechargeable battery. The power supply 202 also provides power to the implanted unit 104 via the inductive coil 212. In one example, the power supply 202 is a battery that can be charged wirelessly, such as through inductive charging. In another example, the power supply 202 is not a replaceable or rechargeable battery and is configured to provide power to the components of the external unit 200 for the operational lifespan of the external unit 200.

The audio transducer 204 receives the sound 110 from a source in an environment and sends a sound signal to the sound processor 208 that includes information indicative of the sound 110. In an example in which the external unit 200 is a component of a cochlear implant, the audio transducer 204 is a microphone, such as an omnidirectional microphone. In another example, the external unit 200 is a component of a bone conduction device, an auditory brain stem implant, a direct acoustic stimulation device, a middle ear implant, or any other hearing prosthesis now known or later developed that is suitable for assisting a recipient of the hearing prosthesis 100 in the perceiving the sound 110. In this example, the audio transducer 204 is an omnidirectional microphone, a directional microphone, an electro-mechanical transducer, or any other audio transducer now known or later developed suitable for use in the type of hearing prosthesis employed. Furthermore, in other examples the audio transducer 204 includes one or more additional audio transducers.

The data storage 206 includes any type of non-transitory, tangible, computer readable media now known or later developed configurable to store program code for execution by a component of the external unit 200 and/or other data associated with the external unit 200. The data storage 206 stores information used by the sound processor 208 to process the sound signal and/or the control processor 218 to determine an operating mode of the external unit 200. The data storage 206 may also store one or more computer programs executable by the sound processor 208 and/or the control processor 218.

The sound processor 208 is configured to determine a stimulation signal suitable for causing the implanted unit 104 to deliver a stimulus to a body part in one of the recipient's auditory pathways. In one example, the sound processor 208 includes one or more digital signal processors. In another example, the sound processor 208 includes any processor or combination of processors now known or later developed suitable for processing the sound 110 and generating the stimulation signal. Additionally, the sound processor 208 may include additional hardware for processing the sound signal, such as an analog-to-digital converter and/or one or more filters.

The sound processor 208 determines the stimulation signal by processing the sound signal received from the audio transducer 204. The stimulation signal includes information indicative of a stimulus current for one or more of the electrodes included on the electrode array 106. The sound processor 208 also receives the telemetry signal 114 from the transceiver 210. The sound processor 208 uses the telemetry signal 114 to determine whether the implanted unit 104 is operating properly, and the sound processor 208 may adjust a subsequent stimulation signal based on the information included in the telemetry signal 114.

The transceiver 210 is configured to send the modulated power signal 112 to and receive the telemetry signal 114 from the implanted unit 104. The transceiver 210 communicates with the implanted unit 104 using a modulation scheme. In one example, the transceiver 210 communicates with the implanted unit 104 using a time-division multiple-access (TDMA) modulation scheme. In another example, the transceiver 210 uses any modulation scheme now known or later developed suitable for modulating communications between the transceiver 210 and the implanted unit 104.

The transceiver 210 is also configured to transmit a command signal to an electronic device. In one example, the transceiver 210 includes one or more components configured to communicate with the implanted unit 104 and one or more additional components configured to transmit the command signal.

The transceiver 210 receives the stimulation signal from the sound processor 208, encodes the stimulation signal, and generates the modulated power signal 112 by modulating the power signal based on the stimulation signal. The transceiver 210 inductively transmits the modulated power signal 112 to the implanted unit 104 via the inductive coil 212 according to the modulation scheme. The transceiver 210 also inductively receives the telemetry signal 114 from the implanted unit 104 via the inductive coil 212. The inductive coil 212 is constructed of any material or combination of materials suitable for inductively transmitting the modulated power signal 112 to and inductively receiving the telemetry signal 114 from the external unit 102.

Additionally, the transceiver 210 is configured to receive a command request from the user interface 220. The transceiver 210 generates a command signal based on the command request, and transmits the command signal to the electronic device via the antenna 214. In one example, the transceiver 210 and the antenna 214 are configured to transmit the command signal in the radio frequency (RF) spectrum, such as at a frequency of about 2.4 GHz. In another example, the transceiver 210 and the antenna 214 are configured to transmit the command signal according to an industry standard, such as a Bluetooth® standard, a WiFi® standard, or any other standard suitable for transmitting the command signal. In another example, the transceiver 210 and the antenna 214 are configured to transmit the command signal at a different frequency in the electromagnetic spectrum. In yet another example, the transceiver 210 is configured to transmit the command signal in a medium other than the electromagnetic spectrum. In this example, the antenna 214 is replaced with a component capable of transmitting the command signal in the medium. For instance, the transceiver 210 may send the command signal to the electronic device via a wired connection, in which case the antenna 214 is replaced with a wired interface module.

The sensor 216 is configured to receive an indication that the external unit 200 is coupled to the implanted unit 104. In one example, the sensor 214 includes a component configured to receive an indication of a magnitude of a magnetic field. When the external unit 200 is coupled to the implanted unit 104, the magnet 232 and a magnet included in the implanted unit 104 create a magnetic field. The component of the sensor 214 receives the indication of the magnitude of the magnetic field and sends a coupling signal that includes information indicative of the magnitude of the magnetic field to the control processor 218. In another example, such as an example in which the control processor 218 determines the operating mode of the external unit 200 based on the telemetry signal 114, the external unit 200 does not include the sensor 216.

The control processor 218 determines the operating mode of the external unit 200. The control processor 218 determines the operating mode by determining whether the external unit 200 is coupled to the implanted unit 104, perhaps by performing one or more of the steps of the method described herein with respect to FIG. 5. In one example, the control processor 218 uses the coupling signal to determine the operating mode of the external unit 200. In another example, the control processor 218 uses the telemetry signal 114 to determine the operating mode of the external unit 200.

The user interface 220 is configured to receive a command request from the recipient (or another user). In one example, the user interface 220 includes one or more buttons, such as the buttons 120-126, that correspond to one or more command requests. In another example, the user interface 220 includes a touch screen. The user interface 220 displays one or command requests on the touch screen, and the recipient interacts with the touch screen to select one of the command requests. The user interface 220 identifies a selected command request based on the recipient's interaction and sends the selected command request to the transceiver 210 for transmission to the electronic device. The recipient may also interact with user interface 220 in order to associate the external unit 200 with the electronic device, which may be accomplished using any method or means now known or later developed.

Figure 2B:
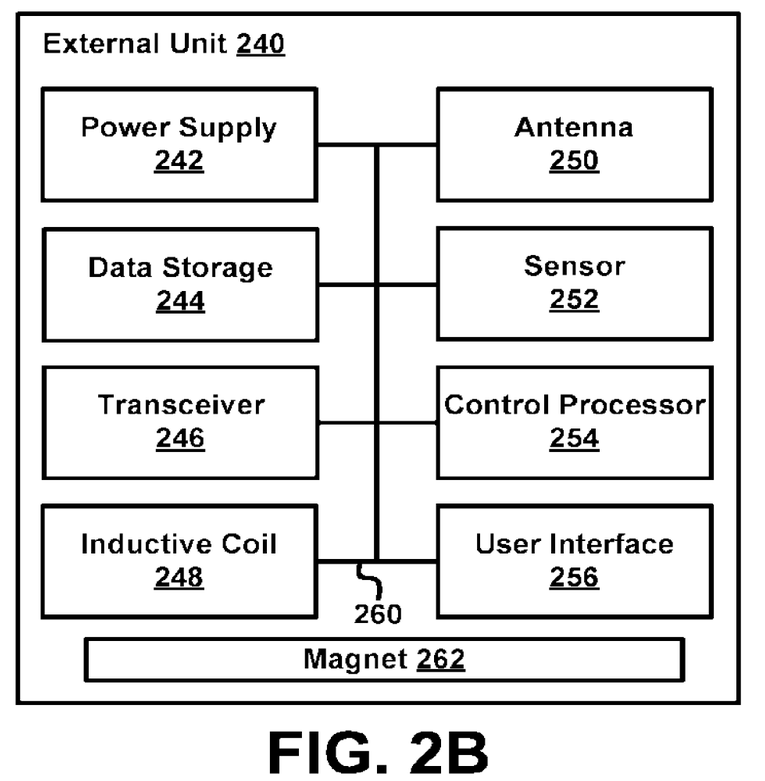
FIG. 2B is a block diagram of an external unit depicted in FIG. 1B, according to an example.

The external unit 200 is also one example of the external unit 132 depicted in FIG. 1B, such as in an example in which the implanted unit 134 depicted in FIG. 1B is configured to both generate and receive the stimulation signal. FIG. 2B is a block diagram of an external unit 240. The external unit 240 is an example of the external unit 132 in a configuration in which the implanted unit 134 is not configured to receive the stimulation signal. The external unit 240 includes a power supply 242, a data storage 244, a transceiver 246, an inductive coil 248, an antenna 250, a sensor 252, a control processor 254, and a user interface 256, all of which are connected either directly or indirectly via circuitry 260. The external unit 240 also includes a magnet 262.

The components of external unit 240 are the same as or are substantially similar to the similarly named components described with respect to FIG. 2A. In one example, because the external unit 240 includes fewer components than the external unit 200, the power supply 242 includes a larger power source than the power supply 202 depicted in FIG. 2A. The larger power source may increase an amount of time between charges, thus allowing the implanted unit 134 to operate for longer periods of time.

Figure 3A:
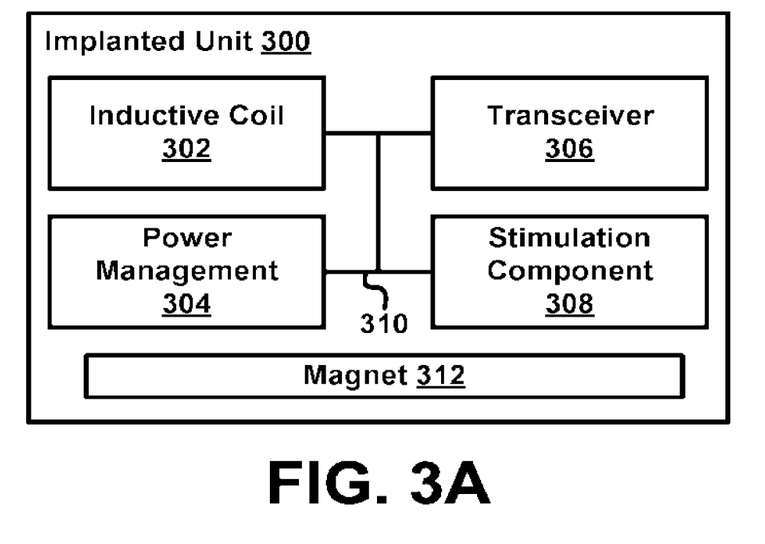
FIG. 3A is a block diagram of an implanted unit depicted in FIG. 1A, according to an example.

FIG. 3A is a block diagram of an implanted unit 300 of a hearing prosthesis. The implanted unit 300 is one example of the implanted unit 104 depicted in FIG. 1A. The implanted unit 300 includes an inductive coil 302, power management 304, a transceiver 306, and a stimulation component 308, all of which are connected directly or indirectly via circuitry 310. The implanted unit 300 also includes a magnet 312, which is used to couple the implanted unit 300 with an associated external unit, such as the external unit 102 depicted in FIG. 1A. For illustrative purposes, the implanted unit 300 is the implanted unit 104 depicted in FIG. 1A.

The inductive coil 302 receives the modulated power signal 112 from the external unit 102. The inductive coil 302 is constructed of any biocompatible material or combination of materials suitable for inductively receiving power from the external unit 102. The inductive coil 302 transfers the power signal to the power management 304. The power management 304 distributes power to the components of the implanted unit 300. In one example, the power management 304 includes a component suitable for separating the modulated power signal 112 into a stimulation signal and a power signal.

Figure 3B:
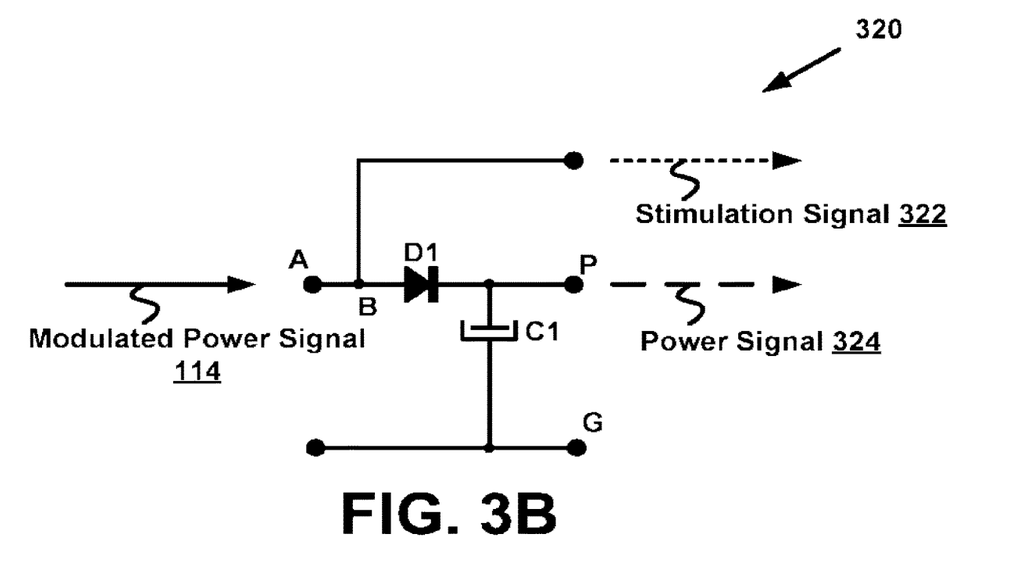
FIG. 3B is a an electrical diagram of a component configured to separate a power signal and a data signal, according to an example.

FIG. 3B is an electrical diagram of a component 320 configured to separate the modulated power signal 114 into a stimulation signal 322 and a power signal 324. The component 320 includes a rectifier formed by a diode D1 and a capacitor C1. The stimulation signal 322 is extracted from the modulated power signal 114 at a point B upstream of the diode D1. The rectifier removes the stimulation signal 322 from the modulated power signal 114, and the power signal 324 is extracted at terminal P with respect to the reference ground G.

Returning to FIG. 3A, the transceiver 306 receives, decodes, and transfers the stimulation signal to the stimulation component 308. The stimulation component 308 generates a stimulus based on the stimulation signal. In one example, the stimulation component 308 includes a first subcomponent configured to generate the stimulus and a second subcomponent configured to deliver the stimulus to a body part, such as a cochlea, an auditory nerve, a brain, and any other organ or body part capable of assisting a recipient in perceiving at least a portion of the sound 110. The first subcomponent generates the stimulus and sends the stimulus to the second component. The second subcomponent delivers the stimulus to the body part of the user.

In an example in which the implanted unit 300 is a component of cochlear implant, the stimulation component 308 includes a signal generator and the electrode array 106. The signal generator generates an electrical signal based on the stimulation signal and sends the electrical signal to the electrode array 106. The electrical signal causes one or more of the electrodes included on the electrode array 106 to deliver one or more electrical stimuli to a portion of the recipient's cochlea. The one or more electrical stimuli cause the cochlea to stimulate an auditory nerve, thereby allowing the recipient to perceive at least a portion of the sound 110.

The stimulation component 308 also generates the telemetry signal 114. In one example, the stimulation component 308 includes a third subcomponent configured to monitor a plurality of parameters associated with generating and delivering the stimulus. The plurality of parameters may include an output voltage, an output current, a line impedance, and/or any other parameter associated with generating and delivering the stimulus. The third subcomponent generates the telemetry signal 114, which includes telemetry data based on one or more parameters included in the plurality of parameters. The stimulation component 308 sends the telemetry signal 114 to the transceiver 306, and the transceiver 306 encodes and transmits the telemetry signal 114 to the external unit 102 according to the modulation scheme.

Figure 3C:
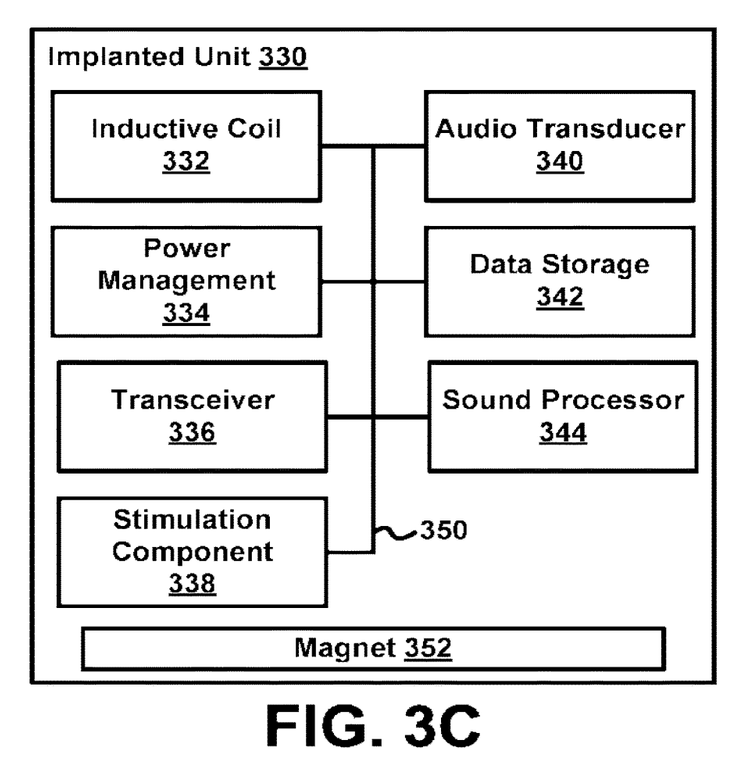
FIG. 3C is a block diagram of an implanted unit depicted in FIG. 1B, according to an example.

FIG. 3C is a block diagram of an implanted unit 330. The implanted unit 330 is one example of the implanted units 104, 134 depicted in FIGS. 1A and 1B. The implanted unit 330 includes an inductive coil 332, power management 334, a transceiver 306, a stimulation component 338, an audio transducer 340, a data storage 342, and a sound processor 344, all of which are connected either directly or indirectly via circuitry 350. The implanted unit 330 also includes a magnet 352, which is used to couple the external unit 300 with an associated external unit, such as the external unit 102 depicted in FIG. 1A. For illustrative purposes, the implanted unit 330 is the implanted unit 134 depicted in FIG. 1B.

The implanted unit 330 is a component of a totally implantable hearing prosthesis. Thus, the implanted unit 330 is configured to receive the sound 110, generate a stimulation signal based on the sound 110, generate a stimulus based on the stimulation signal, and deliver the stimulus to the recipient. The implanted unit 330 is also configured to receive the power signal 142 from the external unit 132. In one example, the implanted unit 330 is further configured to receive a modulated power signal, such as the modulated power signal 112 described with respect to FIGS. 1A and 2A. In this example, the implanted unit 330 is configured to generate the stimulus based on the modulated power signal 112 when the modulated power signal 112 is received. Additionally, the implanted unit 330 may be configured to transmit a telemetry signal to the external unit 132.

The inductive coil 332, the power management 334, the transceiver 336, and the stimulation component 338 are the same as or are substantially similar to the inductive coil 302, the power management 304, the transceiver 306, and the stimulation component 308 described with respect to FIG. 3A. Similarly, the audio transducer 340, the data storage 342, and the sound processor 344 are the same as or are substantially similar to the audio transducer 204, the data storage 206, and the sound processor 208 described with respect to FIG. 2A.

In one example, the power management 334 includes an independent power supply, such as a rechargeable battery. In this example, the power management 334 includes one or more components configured to monitor an amount of charge stored in the power supply. A portion of the power signal 324 is used to charge the power supply when the power supply has less than a full charge. In an absence of a modulated power signal, the power management 334 uses the power supply to provide power to the components of the implanted unit 300.

In another example, the implanted unit 330 is configured to operate in two operating modes. In this example, the implanted unit 330 is paired with an external unit configured to transmit a stimulation signal, such as the external unit 200 described with respect to FIG. 2A. The implanted unit 330 operates in a first operating mode when the external unit is coupled to the implanted unit 330. In the first operating mode, the implanted unit 330 receives the stimulation signal from the external unit via the inductive coil 332. Thus, the implanted unit 330 does not process incoming sound when operating in the first operating mode. Additionally, the implanted unit 330 sends the telemetry signal to the external unit via the inductive coil 332 when operating in the first operating mode.

When the implanted unit 330 is not coupled to the external unit, the implanted unit 330 operates in a second operating mode. In the second operating mode, the audio transducer 340 receives incoming sounds, and the sound processor 344 generates the stimulation signal based on the incoming sounds. The transceiver 336 may also be configured to transmit and receive signals from the external unit when operating in the second operating mode. For example, the transceiver 336 may transmit the telemetry signal to the external unit at a frequency in the electro-magnetic spectrum when operating in the second operating mode. The transceiver 336 may also receive a signal from the external unit that is interleaved with the telemetry signal. In the preceding examples, the transceiver 336 includes a component suitable for transmitting and receiving signals in the electro-magnetic spectrum, such as an antenna.

An external unit of an implanted medical device, such as one of the externals units 102, 132 depicted in FIGS. 1A-1B, may be configured to operate in one of two operating modes. The external unit operates in a first operating mode when the external unit is coupled to an implanted unit, such as one of the implanted units 104, 134 depicted in FIGS. 1A-1B. The external unit operates in a second operating when the external unit is not coupled to the implanted unit. A method for determining the operating mode of an external unit is described herein with respect to FIG. 5.

In the first operating mode, the external unit communicates with the implanted unit. FIGS. 1A and 1B illustrate the external units 102, 132 operating in the first operating mode, respectively. Thus, the external unit 102 transmits the modulated power signal 112 when operating in the first operating mode, and the external unit 132 transmits the power signal 142 when operating in the first operating mode. In the second operating mode, the external unit is configured to transmit a command signal at a frequency in an electromagnetic spectrum. The external unit transmits may transmit the command signal to an electronic device or the implanted unit.

Figure 4A:
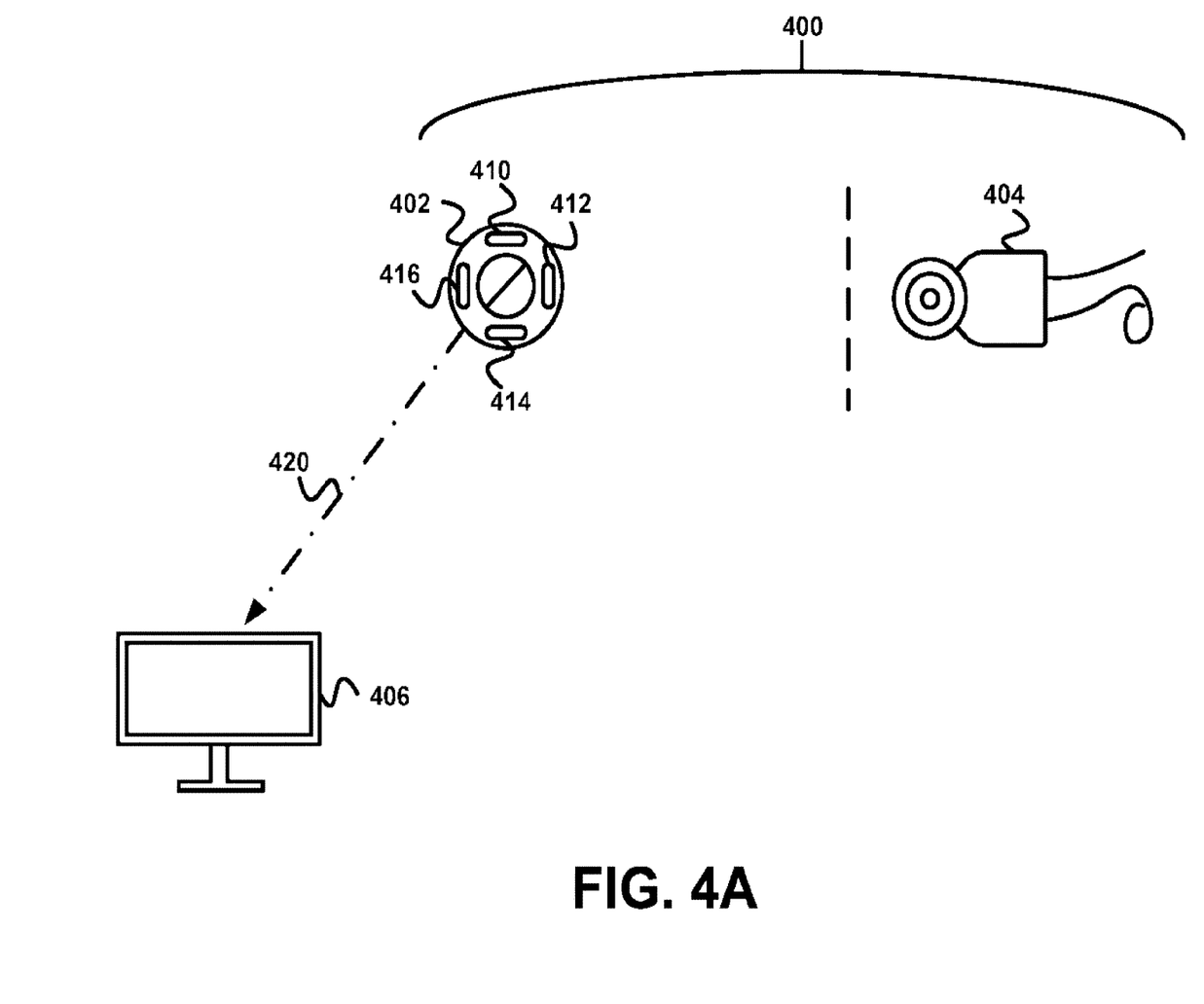
FIG. 4A illustrates a hearing prosthesis that include an external unit operating in a second operating mode, according to a first example.

FIG. 4A illustrates a first example in which an external unit of a hearing prosthesis operates in a second operating mode. FIG. 4A includes an external unit 402, an implanted unit 404, and an electronic device 406. In the second operating mode, the external unit 402 does not communicate with the implanted unit 404. Thus, in an example in which the external unit 402 is the external unit 102 depicted in FIG. 1A, the external unit 402 does not transmit the modulated power signal 112 to the implanted unit 404 when operating in the second operating mode. Similarly, in an example in which the external unit is the external unit 132 depicted in FIG. 1B, the external unit 402 does not transmit the power signal 142 to the implanted unit 404. Rather than transmitting a signal to the implanted unit 404, the external unit 402 transmits a command signal 420 to the electronic device 406. The electronic device 402 may be a television, a Blu-ray® player, a digital video disc (DVD) player, a digital video recorder (DVR), a receiver, or a similar electronic device.

In one example, the external unit 402 operates as a remote control for the electronic device 406 when operating in the second operating mode. The external unit 402 transmits the command signal 420 to the electronic device 402 in response to the recipient pressing one of the buttons 410-416. The buttons 410-416 are the same as or are substantially similar to the buttons 120-126 and/or the buttons 150-156 depicted in FIGS. 1A and 1B, respectively. Each of the buttons 410-416 corresponds to a specific function or command that the electronic device 402 can perform. Upon pressing one of the buttons 410-416, such as a first button 410, the external unit 402 identifies a selected function corresponding to the first button 410. The external unit 402 subsequently generates and transmits the command signal 420, which includes instructions for causing the electronic device 406 to perform the selected function. The electronic device 406, upon receiving the command signal, performs the selected function.

In FIG. 4A, the external unit 402 is depicted as transmitting the command signal to the electronic device 406 wirelessly. In another example, the external unit 402 is connected to the electronic device 406 via a wired connection, such as a USB connection. In this example, the external unit 402 sends the command signal to the electronic device 406 via the wired connection. This may facilitate charging the power supply of the external unit 402 from the external unit 406 while still permitting the user to interact with the electronic device 406 via the buttons 410-416.

Figure 4B:
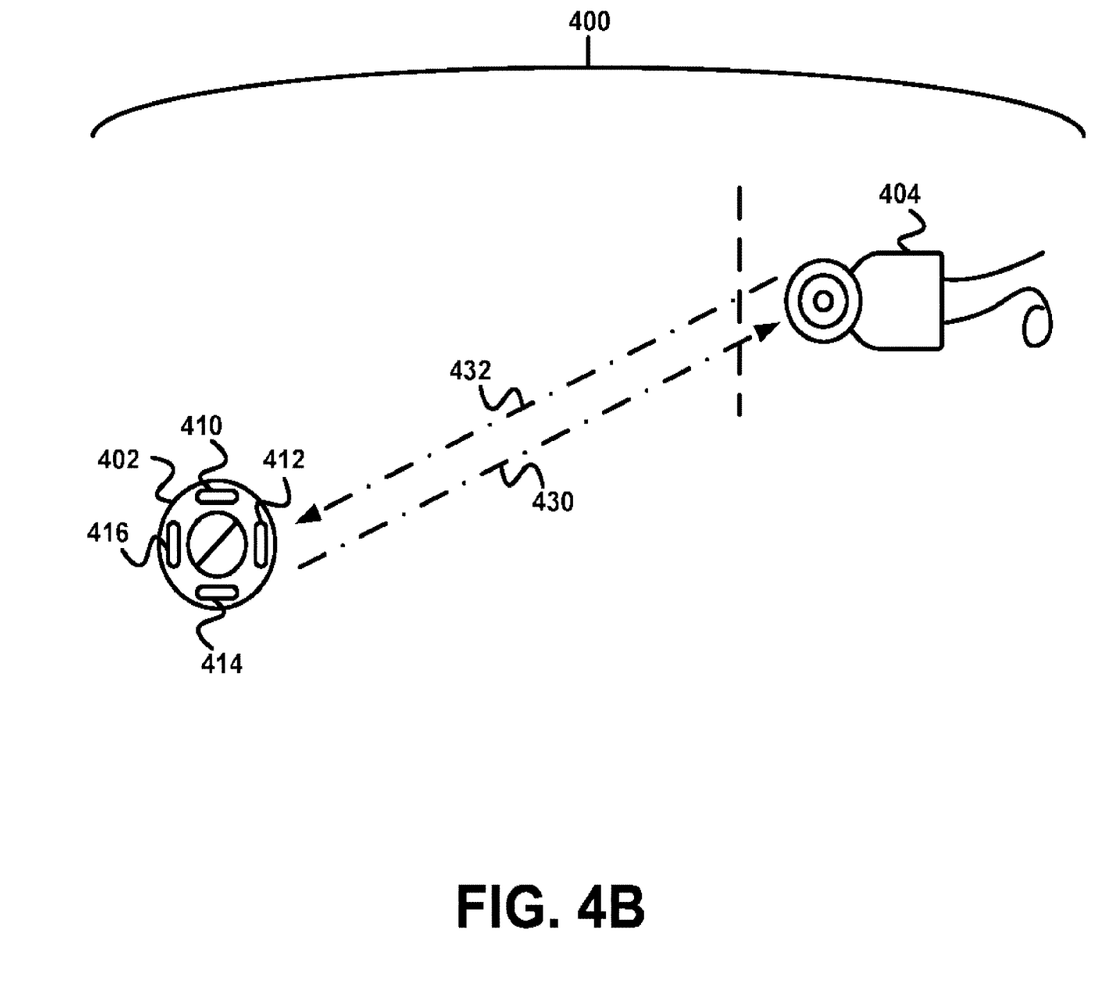
FIG. 4B illustrates a hearing prosthesis that include an external unit operating in a second operating mode, according to a second example

FIG. 4B illustrates a second example in which an external unit of a hearing prosthesis operates in a second operating mode. In FIG. 4B, the external unit 402 communicates with the implanted unit 404 in the second operating mode. In this example, the user, who may be the recipient, can control the implanted unit 404 while the external unit 402 is not coupled to the implanted unit 404. For instance, the user can control a function of the implanted unit 404 when the external unit 402 is charging.

The external unit 402 sends a command signal 430 to the implanted unit 404. The command signal 430 is the same as or is substantially similar to the command signal 420 depicted in FIG. 4A. That is, the command signal 430 includes information indicative of instructions for causing the implanted unit 404 to perform a function. The implanted unit 404, upon receiving the command signal 430, performs the function. In another example, the implanted unit 402 includes the stimulation signal in the command signal 430.

The implanted unit 404 sends a telemetry signal 432 to the external unit 402 when the external unit is in the second operating mode. In this example, the implanted unit 404 determines that external unit 402 is not coupled to implanted unit 404, perhaps by determining an absence of a magnetic field. Upon determining that the external unit 402 is operating in the second operating mode, the implanted unit 404 interleaves transmissions of the telemetry signal 432 with transmissions of the command signal 430. The implanted unit 430 may also include an indication that the implanted unit 430 performed a function requested in a prior transmission of the command signal 430.

The external unit 402 and the implanted unit 404 transmit the command signal 430 and the telemetry signal 432, respectively, at a frequency in the electromagnetic spectrum. In one example, a transmission range of the command signal 430 and the telemetry signal 432 is about three meters. In another example, the transmission range of the command signal 430 and/or the telemetry signal is more or less than three meters, such as about one meter or about ten meters.

Figure 5:
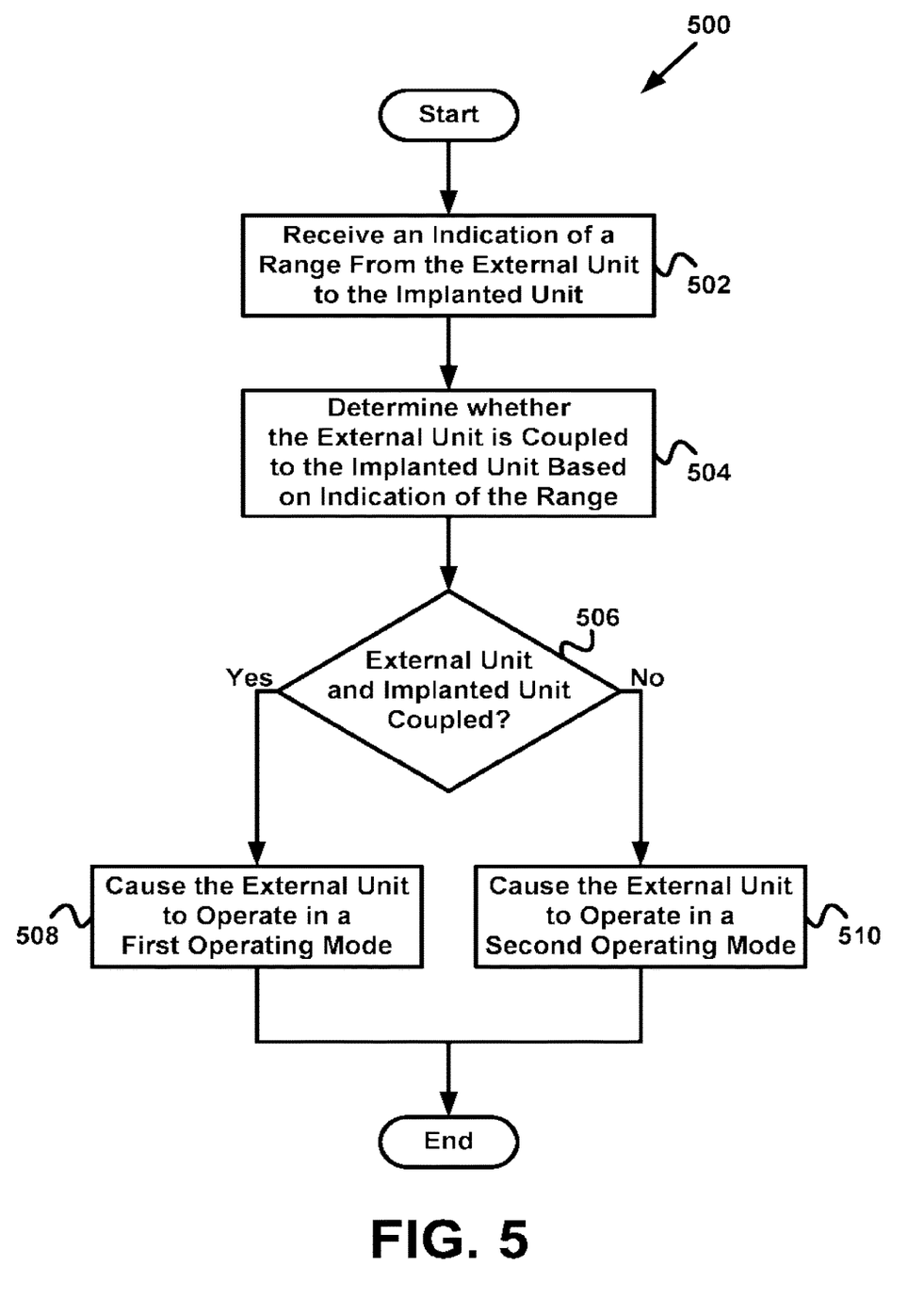
FIG. 5 is a flow diagram for determining an operating mode of an external unit of a hearing prosthesis, according to an example.

FIG. 5 is a flow diagram of a method 500. A processor, such as one of the controls processors 218, 254 depicted in FIGS. 2A-2B, performs the steps of one or more blocks of the method 500 to determine an operating mode of an external unit of an implanted medical device. While the hearing prosthesis 100, the external unit 200, and the implanted unit 300 are described for purposes of illustrating the method 500, it is understood that other devices may be used.

At block 502, the method 500 includes receiving an indication of a range from the external unit to the implanted unit. In one example, the control processor 218 receives the coupling signal from the sensor 216. The coupling signal includes information indicative of a magnitude of a magnetic field created by the magnet 232 and the magnet 312. In another example, the indication of the range is the telemetry signal 114. Because the telemetry signal is transmitted via a near-communication channel, the presence or absence of the telemetry signal provides an indication of the proximity of the external unit 102 to the implanted unit 104.

At block 504, the method 500 includes determining whether the external unit is coupled to the implanted unit based on the indication of the range. In one example, the control processor 218 determines whether the magnitude of the magnetic field is above a threshold magnitude. If the control processor 218 determines that the magnitude is above the threshold magnitude, the control processor 218 determines that the external unit 102 is coupled to the implanted unit 104. If the control processor 218 determines that the magnitude is below the threshold magnitude, the control processor 218 determines that the external unit 102 is not coupled to the implanted unit 104.

In another example, the control processor 218 determines whether the external unit 102 is coupled to the implanted unit 104 by determining whether the external unit 102 received the telemetry signal 114. If the control processor 218 determines that the external unit 102 received the telemetry signal 114, the control processor 218 determines that the external unit 102 is coupled to the implanted unit 104. If the control processor 218 determines that the external unit 102 did not receive the telemetry signal 114, the control processor 218 determines that the external unit 102 is not coupled to the implanted unit 104.

At block 506, the method 500 includes a decision point. If the control processor 218 determined that external unit 102 is coupled to the implanted unit 104, the control processor 508 causes the external unit 102 to operate in the first operating mode, as described with respect to FIGS. 1A and 1B, at block 508. If the control processor 218 determined that the external unit 102 is not coupled to the implanted unit 104, the control processor causes the external unit 102 to operate in the second operating mode, as described with respect to FIG. 4, at block 510.

Once the steps of either block 508 or block 510 are complete, the method 500 ends. In one example, the control processor 218 performs the method 500 at a given interval in order to determine whether a status of the coupling between the external unit 102 and the implanted unit 104 has changed. In another example, the control processor 518 performs the method 500 upon identifying a change in the indication of the range, such as a change in the magnitude of the magnetic field or a change in the status of receiving the telemetry signal As noted above, implanted medical devices other than hearing prostheses may implement one or more steps of the method 500 in order to determine an operating mode of the implanted medical device. For instance, a vestibular implant may include an implanted unit and an external unit. A component of the external unit, such as a processor, may implement one or more steps of the method 500 to determine an operating mode of the external unit. Other examples are also possible.

With respect to any or all of the flow diagrams, scenarios, and flow charts in the figures and as discussed herein, each step, block and/or communication may represent a processing of information and/or a transmission of information in accordance with example embodiments. Alternative embodiments are included within the scope of these example embodiments. In these alternative embodiments, for example, functions described as steps, blocks, transmissions, communications, requests, responses, and/or messages may be executed out of order from that shown or discussed, including in substantially concurrent or in reverse order, depending on the functionality involved. Further, more or fewer steps, blocks and/or functions may be used with any of the message flow diagrams, scenarios, and flow charts discussed herein, and these message flow diagrams, scenarios, and flow charts may be combined with one another, in part or in whole.

A step or block that represents a processing of information may correspond to circuitry that can be configured to perform the specific logical functions of a herein-described method or technique. Alternatively or additionally, a step or block that represents a processing of information may correspond to a module, a segment, or a portion of program code (including related data). The program code may include one or more instructions executable by a processor for implementing specific logical functions or actions in the method or technique. The program code and/or related data may be stored on any type of computer-readable medium, such as a storage device, including a disk drive, a hard drive, or other storage media.

The computer-readable medium may also include non-transitory computer-readable media such as computer-readable media that stores data for short periods of time like register memory, processor cache, and/or random access memory (RAM). The computer-readable media may also include non-transitory computer-readable media that stores program code and/or data for longer periods of time, such as secondary or persistent long term storage, like read only memory (ROM), optical or magnetic disks, and/or compact-disc read only memory (CD-ROM), for example. The computer-readable media may also be any other volatile or non-volatile storage systems. A computer-readable medium may be considered a computer-readable storage medium, for example, or a tangible storage device.

Moreover, a step or block that represents one or more information transmissions may correspond to information transmissions between software and/or hardware modules in the same physical device. However, other information transmissions may be between software modules and/or hardware modules in different physical devices.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method, comprising:
operating an external component of an auditory prosthesis in a first mode to communicate with an implantable component of the auditory prosthesis via a first communications channel, wherein in the first mode the external component is coupled to the implantable component and the first communication channel is used for a first set of functions;
determining, at the external component, that the external component is no longer coupled to the implantable component; and
in response to determining that the external component is no longer coupled to the implantable component, operating the external component in a second mode to communicate with the implantable component via a second communication channel that is different from the first communication channel and is used for a second set of functions that are a subset of the first set of functions.

2. The method of claim 1, wherein the first set of functions includes transmission of a stimulation signal to the implantable component for delivery to a recipient of the auditory prosthesis.

3. The method of claim 2, wherein the second set of functions do not include transmission of a stimulation signal to the implantable component.

4. The method of claim 1, wherein the first and second set of functions each include a plurality of sound processing command functions that modify a stimulation signal generated by the auditory prosthesis.

5. The method of claim 1, wherein determining that the external component is no longer coupled to the implantable component comprises:
receiving an input signal from a user interface.

6. The method of claim 1, wherein the external component and the implantable component each comprise magnets configured to magnetically couple the external component to the implantable component in the first mode, and wherein determining that the external component is no longer coupled to the implantable component comprises:
determining that the external component is no longer magnetically coupled to implantable component.

7. The method of claim 1, wherein determining that the external component is no longer coupled to the implantable component comprises:
determining, at the external component, a distance between the external component and the implantable component; and determining that the distance is greater than a predetermined threshold.

8. An external component of an auditory prosthesis comprising:
- a microphone configured to receive sound signals;
- a sound processor connected to the microphone and configured to convert the sound signals into stimulation signals for use at an implantable component of the auditory prosthesis;
- a magnetic induction coil;
- an antenna; and
- at least one transceiver configured to:
  - when the external component is coupled to the implantable component, communicate stimulation signals to the implantable component via the magnetic induction coil, and
  - only when the external component is not coupled to the implantable component, communicate control commands via the antenna to one or more of the implantable component or a second electronic device that is separate from the auditory prosthesis.

9. The external component of claim 8, wherein the external component comprises a battery, and wherein when the external component is coupled to the implantable component the external component is configured to transfer power from the battery to the implantable component concurrently with the stimulation signals via the magnetic induction coil.

10. The external component of claim 8, wherein the external component comprises a user interface configured to receive user inputs, and wherein when the external component is not coupled to the implantable component the external component is configured to generate the control commands based on the user inputs received via the user interface prior to communicating the control commands to the one or more of the implantable component or a second electronic device via the antenna.

11. The external component of claim 8, further comprising a control processor configured to determine whether the external component is coupled to the implantable component.

12. The external component of claim 11, further comprising a sensor configured to receive an indication of a magnitude of a magnetic field and to provide a coupling signal that includes information indication of the magnetic field to the control processor, wherein the control processor is configured to determine whether the external component is coupled to the implantable component based on the coupling signal.

13. The external component of claim 11, wherein the control processor is configured to determine a distance between the external component and the implantable component and to determine whether the external component is coupled to the implantable component based on the determined distance.

14. The external component of claim 11, wherein the transceiver is configured to receive a telemetry signal from the implantable component via the magnetic induction coil, and wherein the control processor is configured to determine whether the external component is coupled to the implantable component based on at least one of the telemetry signal or an absence of the telemetry signal.

15. An auditory prosthesis comprising:
- an implantable component configured to deliver a stimulus to a recipient of the auditory prosthesis to evoke a hearing percept; and
- a wearable external component configured to:
  - when the external component is coupled to the implantable component, operate in a first mode to communicate with the implantable component via a first communications channel, wherein the first communication channel is used for a first set of functions;
  - determine that the external component is no longer coupled to the implantable component; and
  - in response to determining that the external component is no longer coupled to the implantable component, operate in a second mode to communicate with one or more of the implantable component or a second electronic device that is separate from the auditory prosthesis via a second communication channel that is different from the first communication channel, and wherein the second communication channel is used for a second set of functions that is different from the first set of functions.

16. The auditory prosthesis of claim 15, wherein the first communication channel is a near-field communications channel.

17. The auditory prosthesis of claim 15, wherein the second communication channel is a communications channel operating in a radio-frequency spectrum.

18. The auditory prosthesis of claim 15, wherein when operating in the first mode the external component is configured to deliver power to the implantable component.

19. The auditory prosthesis of claim 15, wherein when operating in the second mode the external component is configured to communicate command functions to the implantable component.

20. The auditory prosthesis of claim 19, wherein the command functions include at least one of a volume command that modifies a perceived volume of the stimulus, and a program command that changes parameters used by the implantable component to generate the stimulus.

21. The auditory prosthesis of claim 15, wherein when operating in the second mode the external component does not transfer power to the implantable component.

22. The auditory prosthesis of claim 15, when operating in the second mode the external component does not transfer communications via the first communications channel.

23. The auditory prosthesis of claim 15, wherein the external component is configured to:
- determine when the external component is not adjacent the implantable component, and
- operate in a second mode in response to determining that the external component is not adjacent the implantable component.

* * * * *